United States Patent [19]
Heacock

[11] Patent Number: 5,673,097
[45] Date of Patent: Sep. 30, 1997

[54] PORTABLE SCANNING LASER OPHTHALMOSCOPE

[76] Inventor: Gregory Lee Heacock, 505 Timber Valley Rd., Atlanta, Ga. 30342

[21] Appl. No.: 631,969

[22] Filed: Apr. 15, 1996

[51] Int. Cl.⁶ ........................................ A61B 3/10
[52] U.S. Cl. ................... 351/218; 351/215; 351/221
[58] Field of Search ........................... 351/218, 215, 351/221, 205, 246

[56] References Cited

U.S. PATENT DOCUMENTS 4,877,322 10/1989 Hill ............................................... 351/221
5,576,780 11/1996 Yancey ......................................... 351/246

*Primary Examiner*—Hung X. Dang
*Attorney, Agent, or Firm*—McAndrews, Held & Malloy, Ltd.

[57] ABSTRACT

A portable scanning laser ophthalmoscope with a wide field of view permits a clinician to directly view the interior of the patient's eye without the use of an external monitor or display. The portable scanning laser ophthalmoscope includes a housing that is sufficiently small to be carried and held by a clinician. The housing contains a source of laser light that is scanned by a scanning system for generating a two-dimensional area of illumination. The housing also includes a battery for providing power to the scanning system. An optical system contained in the housing directs illumination from the scanning system to the patient's eye to illuminate the fundus and also intercepts light reflected by the patient's eye to generate a magnified image of the interior of the patient's eye. The optical system also includes an eyepiece lens through which a clinician looks to directly view the magnified image of the interior of the patient's eye.

32 Claims, 4 Drawing Sheets

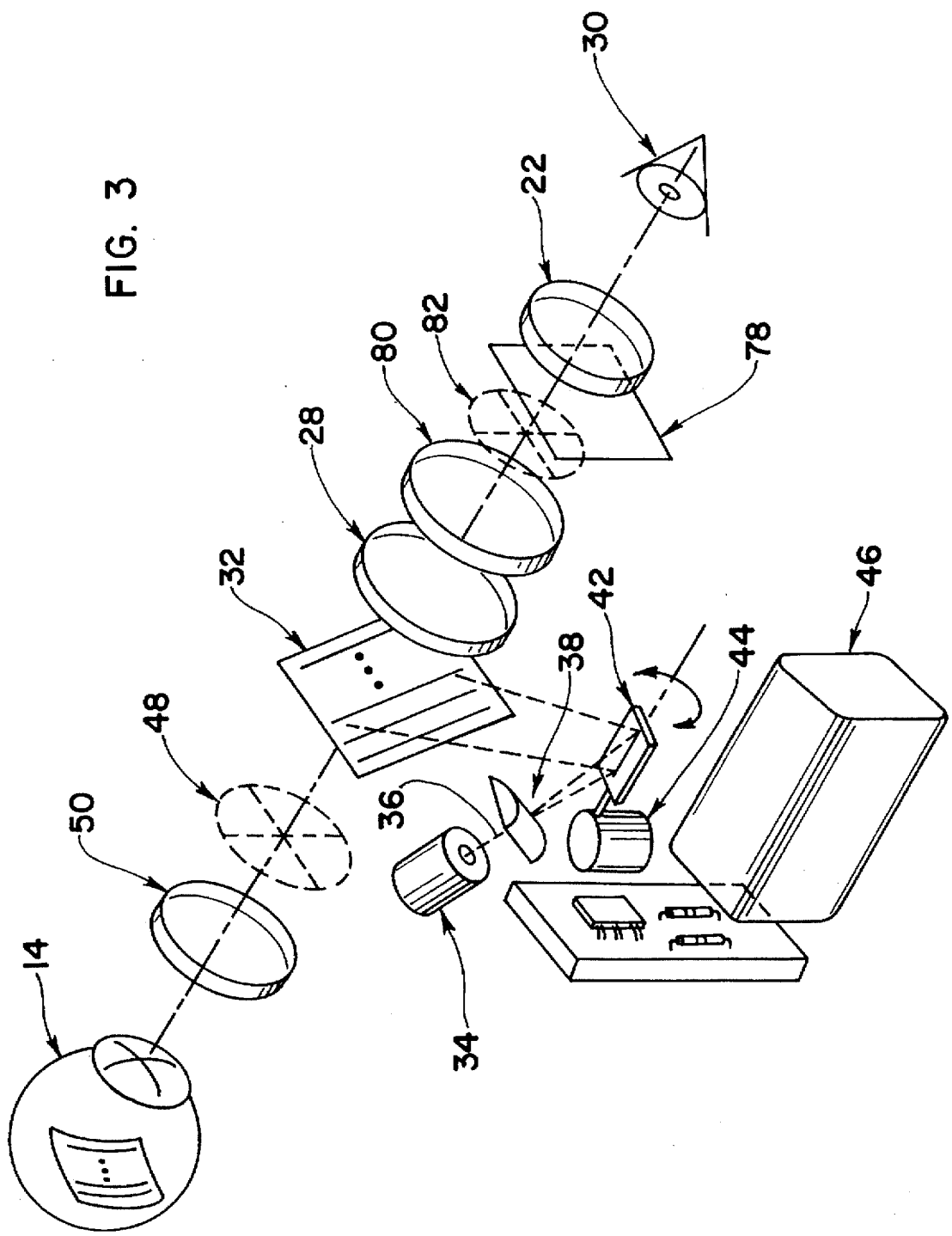

PORTABLE SCANNING LASER OPHTHALMOSCOPE

This is related to U.S. patent application Ser. No. 08/629,584 filed Apr. 9, 1996 entitled Wide Field of View Scanning Laser Ophthalmoscope.

FIELD OF INVENTION

The present invention relates to a scanning laser ophthalmoscope and more particularly to a portable scanning laser ophthalmoscope with a wide field of view that allows a clinician to directly view the interior of the patient's eye without the use of an external monitor.

BACKGROUND OF THE INVENTION

Scanning laser ophthalmoscopes such as shown in Webb U.S. Pat. Nos. 4,765,730; Webb 4,764,006 and Webb 4,768,873 are known to include a turning mirror to direct a laser beam to a multi-faceted rotating polygonal reflector scanner that scans a laser beam in a first direction to form a line of light. A second scanner is employed in the form of a galvanometer reflector scanner to scan the line of light generated by the first scanner in a second direction perpendicular to the first direction of scanning. The scanned light is directed to a patient's eye by a series of focusing mirrors. Light reflected from the patient's eye follows the same path via the scanners and focusing mirrors back to the turning mirror. The turning mirror is small so that the light reflected from the eye passes around it to an optical detector in the form of an avalanche diode. The output of the optical detector is coupled to the display to provide a two dimensional picture of the patient's retina. Although this type of scanning laser ophthalmoscope is capable of producing an image of the patient's retina without requiring the patient's pupil to be dilated with drugs and without requiring contact with the patient's eye, it has several drawbacks. First, the scanned laser light source employed in Webb's scanning laser ophthalmoscope is very bright and leaves the patient dazzled for some time following the diagnostic procedure implemented with the ophthalmoscope. Further, the Webb system is large, complex and very costly. The Webb system also suffers from a small field of view that is on the order of only 30°.

Another type of scanning laser ophthalmoscope is shown in Kobayashi U.S. Pat. No. 4,781,453 that utilizes a first acousto optical modulator for modulating the intensity of a laser beam to project a fixation target. The frequency of the drive signal for the first acousto optical modulator is also varied so as to select, with the use of a lens and device having a slit therein, a single wavelength of a laser beam having a number of wavelengths therein. The single selected wavelength of the laser is then passed to a scanning system. The scanning system includes a second acousto optical modulator that is driven so as to scan the selected wavelength of the laser in a first direction. Prior to scanning, however, the range of the second acousto optical modulator must be changed to accommodate the selected wavelength of the laser. The scanned laser is guided by relay lenses from the second acousto optical modulator to a mirror that is mounted on a galvanometer for scanning the laser in a second direction perpendicular to the scanning direction of the second acousto optical modulator. A small mirror then reflects the scanned light to a patient's eye. The light reflected from the eye passes around the small mirror and is captured by a lens and focused on a photosensor. A filter corresponding to the selected wavelength of the laser is disposed in front of the photosensor to allow passage of the selected light to the sensor. An image of the eye at a depth corresponding to the selected wavelength is stored in a frame memory associated with the selected wavelength, wherein the system includes different frame memories for the different wavelengths that can be selected. The different images stored in the frame memories can be selected via the electronics of the system for individual display in different colors on a color monitor. The Kobayashi ophthalmoscope is an extremely complex device in which the scanning range of the second acousto optical modulator must be changed to accommodate a selected wavelength of the laser light each time a new wavelength is selected via the first acousto optical modulator. Further, the filter disposed in front of the photo sensor must also be changed in accordance with the selected wavelength. The field of view of this scanning laser ophthalmoscope is also small, being on the same order as that described above for the Webb scanning laser ophthalmoscope.

In both the Webb and Kobayashi systems, a mirror is disposed in the optical path of the light reflected from the patient's eye to the detector which causes a shading off effect. This shading off effect is realized as a darkening of the edges of an image feature with a gradual lightening of the image feature towards the center thereof. For example, this effect causes the displayed image of a blood vessel to appear as dark parallel lines with a lighter center therebetween. This effect is further exacerbated by the small aperture diameter employed in the image detection portion of the these systems. This small aperture although eliminating unwanted reflections from detection, brings substantially all of a given scene into focus at the same focal plane. The result is that the image of the patient's fundus appears similar regardless of the wavelength of the laser beam and the portion of the patient's eye at a particular depth therein reflecting the selected wavelength of the light.

Further, the known scanning laser ophthalmoscopes such as described above are large and nonportable. As a result patients must be taken to the instrument for the eye examination which can be difficult with a sick patient that is bedridden. These ophthalmoscopes are also extremely complex and costly due to their optical arrangements and the necessity of image detectors and monitors for displaying an image of the eye.

SUMMARY OF THE INVENTION

In accordance with the present invention, the disadvantages of prior scanning laser ophthalmoscopes have been overcome. The scanning laser ophthalmoscope of the present invention is portable; provides a wide field of view; and allows a clinician to directly view the interior of a patient's eye without the use of an external monitor. The scanning laser ophthalmoscope of the present invention is extremely simplified compared to prior devices and eliminates the shading off effects found in the displayed eye images produced by prior scanning laser ophthalmoscopes.

More particularly, the portable scanning laser ophthalmoscope of the present invention includes a housing that is sufficiently small to be carried and held by a clinician. The housing contains a source of laser light that is scanned by a scanning system for generating a two dimensional area of illumination. The housing also includes a battery for providing power to the scanning system. An optical system contained in the housing directs illumination from the scanning system to the patient's eye to illuminate the fundus and also intercepts light reflected by the patient's eye to generate a magnified image of the interior of the patient's eye. The optical system also includes an eyepiece lens through which a clinician looks to directly view the magnified image of the interior of the patient's eye.

In accordance with another feature of the present invention, shading off in the image captured by the scanning laser ophthalmoscope is prevented by separating the optical path between the patient's eye and the scanning system from the optical path between the patient's eye and the eyepiece lens with a beam splitter that does not block the chief ray reflected at any given position in the patient's eye on its path to the eyepiece lens.

In accordance with another feature of the present invention, the scanning system includes only one scanner with a moveable reflective surface and a passive, stationary optical element. The passive optical element is positioned in a path of the laser light such that the light impinges on the optical element at a point and the optical element generates a line of light from that point. The single scanner with moveable reflective surface is then used to scan the line of light generated by the passive optical element in a direction perpendicular to the line so as to generate the two dimensional area of illumination. Because only a single scanner with a moveable reflective surface is employed as opposed to two such scanners, the scanning laser ophthalmoscope is more rugged than prior devices and more compact, enabling the ophthalmoscope to be portable. Further, because a passive, stationary optical element is employed as opposed to an active optical device, such as an acousto optical modulator that requires a drive signal to scan, the electronics of the present scanning laser ophthalmoscope are again greatly simplified.

In accordance with a further feature of the present invention, a nonsymmetric aspheric lens is employed to focus the illumination light from the illumination system on an area generally proximate to the patient's pupil and to capture light reflected from the patient's eye and to focus that reflected light onto an image plane. This aspheric objective lens which is positioned between the patient's eye and the eyepiece lens greatly simplifies the optical system of the scanning laser ophthalmoscope of the present invention and greatly reduces the optical components thereof.

Further, in accordance with another feature of the present invention, the laser light from the source is polarized in a first direction and a polarizer disposed between the aspheric objective lens and the eyepiece lens is polarized in a second direction that is different from the first direction to pass only desired light to the eyepiece lens. Thus, unwanted reflections are eliminated from the magnified image viewed by the clinician.

These and other advantages and novel features of the present invention, as well as details of an illustrated embodiment thereof, will be more fully understood from the following description and drawings.

BRIEF DESCRIPTION OF THE DRAWING

FIG. 3 is a prospective view of the components of the portable scanning laser ophthalmoscope of FIG. 2.

DESCRIPTION OF THE PREFERRED EMBODIMENT

Figure 1:
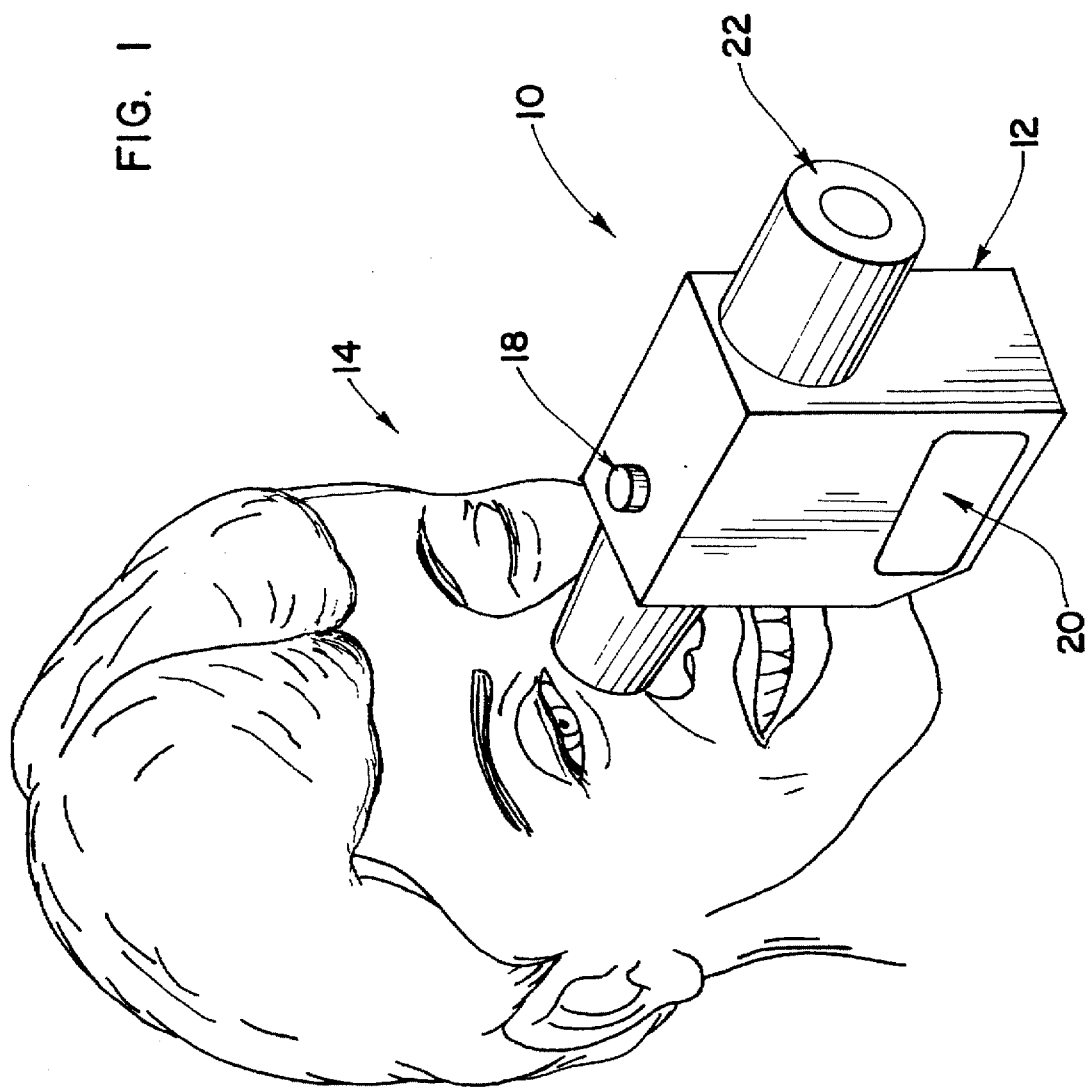
FIG. 1 is a perspective view of a portable scanning laser ophthalmoscope in accordance with the present invention positioned with respect to a patient's eye so that a clinician can view the interior thereof.

A portable scanning laser ophthalmoscope 10 in accordance with the present invention as shown in FIG. 1 includes a housing 12 that is sufficiently small to be carried by a clinician and held in a clinician's hand during an examination of a patient's eye 14. More particularly, during an eye examination, the clinician holds the housing 12 of the scanning laser ophthalmoscope 10 so that a housing portion 16 containing an objective lens is positioned near the patient's eye 14. The clinician then presses an on-off button 18 so as to provide power to a scanning system of the ophthalmoscope 10 from a battery contained within the housing 12. The battery is easily accessible to a user via an access panel 20. When the scanning laser ophthalmoscope is turned on, the scanning system thereof illuminates a two-dimensional area of the interior of the patient's eye 14. Light reflected from the patient's eye due to this illumination is captured by the optical system of the ophthalmoscope 10 so that a magnified image of an interior portion of the patient's eye 14 can be viewed directly by the clinician through an eyepiece lens 22.

Figure 2:
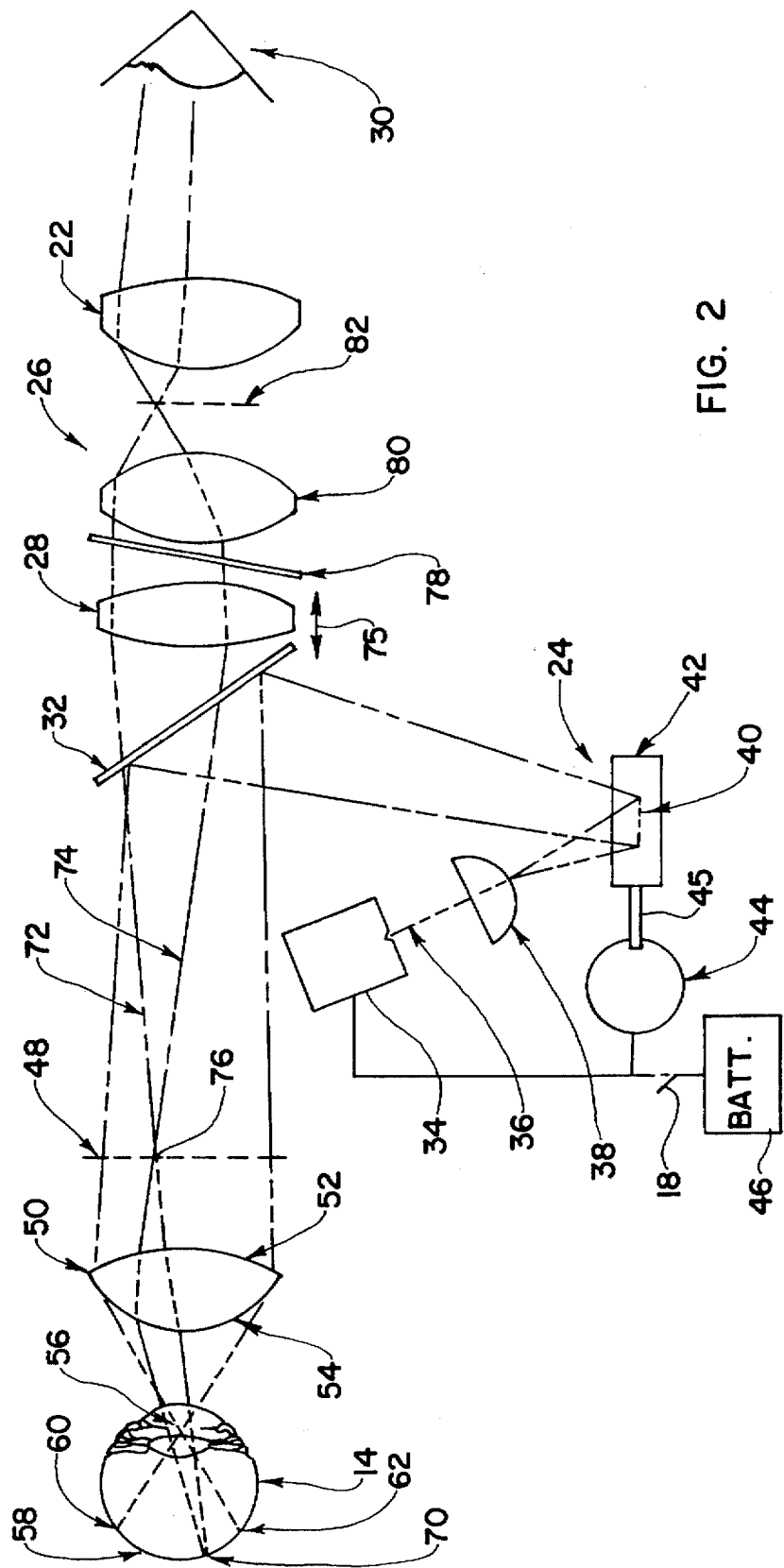
FIG. 2 is a plan view of the portable scanning laser ophthalmoscope of FIG. 1 shown in relation to the patient's eye.

The portable scanning laser ophthalmoscope 10 as shown in detail in FIGS. 2 and 3 includes a scanning system 24 for scanning the two-dimensional area of illumination that illuminates the interior of the patient's eye 14. The scanning laser ophthalmoscope 10 also includes an optical system 26 with a movable field lens 28 to capture light reflected from the patient's eye 14 so that a clinician 30 can view an interior portion of the patient's eye 14 through the eyepiece lens 22. The optical path from the scanning system 24 to the patient's eye is separated from the optical path from the patient's eye to the field lens 28 and eyepiece lens 22 so that in the portable scanning laser ophthalmoscope 10 of the present invention there is no scanner, mirror or other optical element that totally blocks light reflected from the patient's eye 14 in a given region of the optical path to the eyepiece lens 22. This feature illuminates shading off problems of prior scanning laser ophthalmoscopes.

Figure 4A:
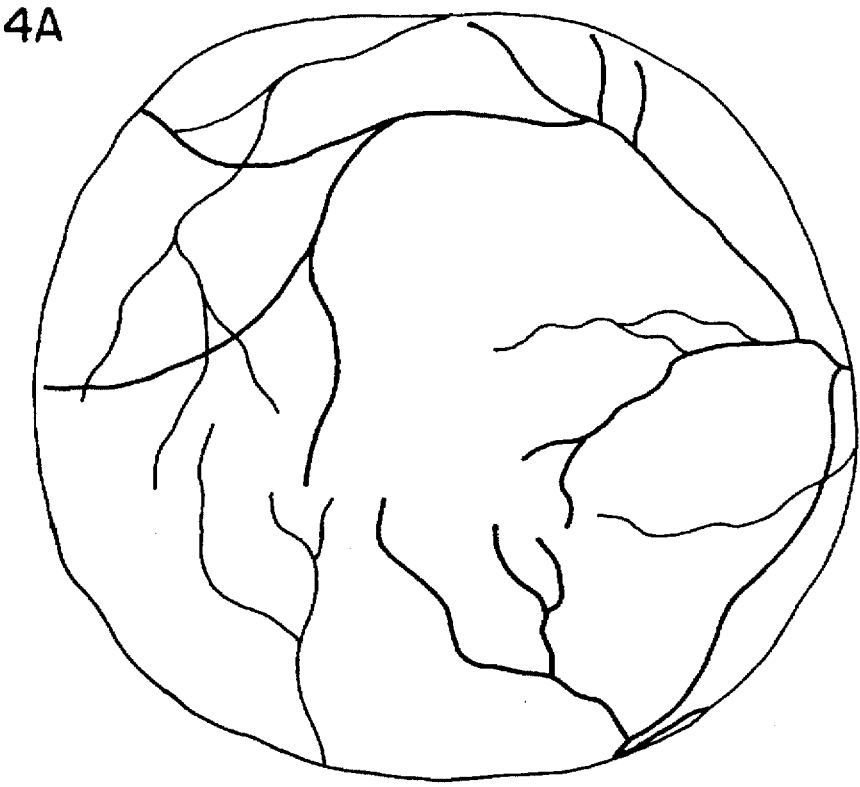
FIGS. 4A and 4B respectively illustrate an image of an eye as viewed via the scanning laser of ophthalmoscope of FIGS. 1–3 and of an eye image displayed with a prior device that produces a shading off effect.

In order to accomplish the separation of the scanning system 24 from the optical path between the patient's eye and the eyepiece lens 22, the scanning laser ophthalmoscope 10 includes a beam splitter 32. The beam splitter 32 is a partially reflecting illumination mirror that reflects at least 25% of the illumination light from the scanning system 24 to the patient's eye 14 while passing therethrough light reflected from the patient's eye 14 so that the interior portion of the patient's eye can be viewed by the clinician through the eyepiece lens 22. It has been found that the shading off effects plaguing prior scanning laser ophthalmoscopes were caused by an optical element such as a scanner or mirror placed in the optical path from the patient's eye to the eye image capturing system. These optical elements block the chief ray from any given image position on its route from the patient's eye to the image capturing optics thereby causing shading off. The present invention eliminates this problem by separating the path to the eyepiece lens 22 from the scanning system 24 and by employing optical elements within the optical path from the patient's eye to the lens 22 that do not block the chief rays from any given image position on their route to the lens 22. As a result, the image of the eye viewed by a clinician with the ophthalmoscope 10 is as shown in FIG. 4A as opposed to an image of the eye as shown in FIG. 4B that has the shading off effect.

Figure 4B:
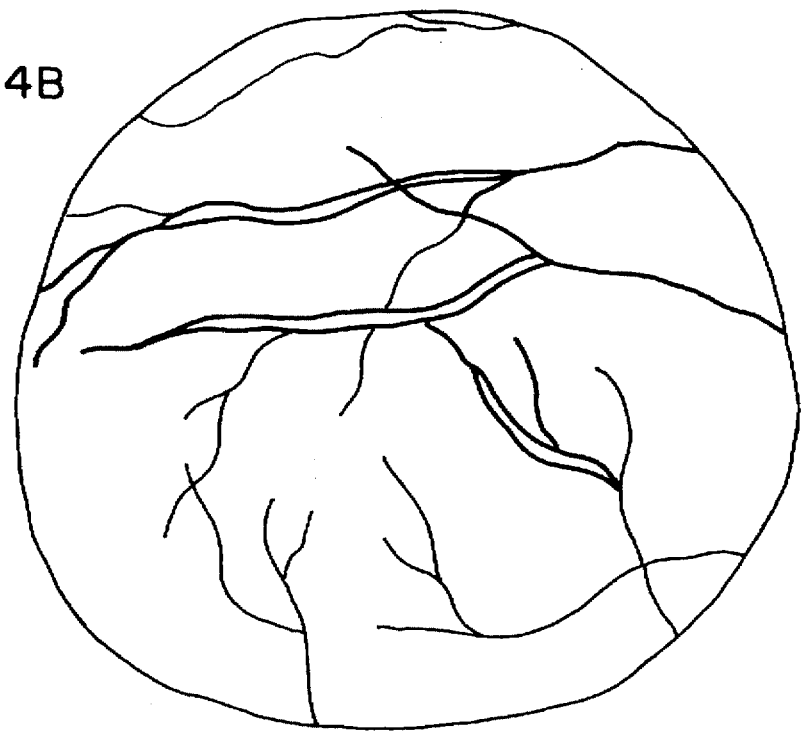

The shading off effect can be seen in FIG. 4B as a darkening of the edges of a feature of the image and as a lightening of the center of the feature. For example, in FIG. 4B the imaged features of blood vessels are shown as dark parallel lines with a gradual lightening towards the center of the blood vessel. This effect is not present in the image displayed by the scanning laser ophthalmoscope 10 of the present invention as depicted in FIG. 4A because the chief ray from any given position in the eye is not blocked on its route to the eyepiece lens 22.

As shown in FIGS. 2 and 3, the scanning system 24 of the ophthalmoscope 10 includes a laser source 34. The laser source 34 generates a laser beam 36 that impinges on a passive, stationary optical element 38 at a point. The passive, stationary optical element 38, which may be a cylindrical lens as shown, generates a line 40 of light from the point of light impinging on the lens 38. The line 40 of laser light is scanned in a direction perpendicular to the direction of the line 40 by a scanner mirror 42 on which the line of light impinges. The scanner mirror 42 is driven by a scanner motor 44 that is coupled to the mirror 42 via a shaft 45. A battery 46 provides power the scanner motor 44 and to the laser source 34 via the on-off switch 18. As the scanner mirror 42 vibrates, it scans the line 40 horizontally across the face of the partially reflective beam splitter 32 as shown in FIG. 3 so that a rectangular shaped area of illumination is generated on the face of the beam splitter 32. The beam splitter 32 reflects the rectangular area of illumination light towards the eye 14 so that it is centered on a real image plane 48 and on a nonsymmetric aspheric objective lens 50. The illumination light as it travels towards the patient's eye 14 is slightly diverging. The weaker surface 52 of the aspheric lens makes the slightly diverging illumination light parallel and directs the illumination light to the stronger surface 54 of the aspheric lens 50. The stronger surface 54 of the aspheric lens focuses the illumination light to a point 56 that is centered on the patient's pupil or generally proximate thereto. The illumination light continues its path until it strikes the retina 58 of the eye 14, thus illuminating an area of the patient's eye within the boundaries of the rays 60 and 62. The use of the passive optical element 38 that converts a point of light impinging thereon into a line of light without an external drive signal applied thereto as required by acousto optic modulators and without movement of an element as in scanning mirrors, substantially simplifies the optical system of the present invention and reduces the size thereof so as to enable the scanning laser ophthalmoscope 10 to be packaged in a portable housing 12.

In order to focus the eye image capturing system 26 onto different areas of a patient's eye 14, the optical system 26 includes the moveable field lens 28. More particularly, as shown in FIGS. 2 and 3, an illuminated point 70 on the fundus 58 of the patient's eye 14 reflects light shown by the rays 72 and 74 wherein the reflected light is captured and focused by the aspheric objective lens 50 to a point 76 on the image plane 48. The light reflected from the patient's eye 14 passes through the beam splitter 32 to the field lens 28. The field lens 28 is moveable in the direction of the arrow 75 so as to change the position of the image plane 48 closer to or farther from the lens 50, thus changing the location of the point 70. The light reflected from the patient's eye passes through the field lens 28 and from there through a polarizer film 78 to an image lens 80. The image lens 80 and field lens 28 form a magnified image 82 of the interior of the patient's eye which is observed by the clinician 30 as he looks into the eyepiece lens 22.

In order to pass only desired light to the eyepiece lens 22, the laser light from the source 34 is polarized in a first direction and the polarizer film 78 of the optical system 26 is polarized in a second direction that is different from the first direction. In particular, the polarizer film 78 is preferably polarized in a direction perpendicular to the polarization of the laser light from the source 34. This polarization of the polarizer film 112 blocks unwanted reflections from the patient's cornea, the aspheric lens 50 and other elements of the system from reaching the image lens 80 and eyepiece lens 22 so that only the randomized reflected image from the interior of the patient's eye passes through the optical system into the eyepiece lens 22.

The aspheric lens 50 of the present invention focuses the illumination light from the illumination system 24 on an area of the patient's eye that is generally proximate to the pupil and the aspheric lens 50 also intercepts light reflected from the patient's eye 14 and focuses the intercepted light onto the image plane 48 that is disposed between the aspheric lens and the eyepiece lens 22. In order to provide such an aspheric lens, each surface 52 and 54 of the lens is preferably described by the polynomial function:

$$f(Y, A_2, A_4, A_6, C, cc) = A_2 Y^2 + A_4 Y^4 + A_6 Y^6 + CY^2/(1 + \sqrt{1 - C^2 cc})$$

where $A_2$, $A_4$ and $A_6$ are constants; C represents the curvature of the surface; and cc represents the conic constant. For the stronger surface 54 of the lens 50, these values should be within the following ranges:

$0.0 < A_2 < 0.003$ $-0.02 < A_4 < 0.02$ $-0.01 < A_6 < 0.01$ $-0.1 < C < 0.0$ $-2.0 < cc < 1.0$

For the weaker surface 52 of the lens 50 these values should be within the following ranges:

$-0.003 < A_2 < 0.0$ $0.0 < A_4 < 0.001$ $-0.001\ A_6 < 0.001$ $0.03 < C < 0.06$ $-2.0 < cc < 0.0$

Further the curvature C of the weaker surface 52 is preferably greater than $-\frac{1}{2}$ times the curvature C of the stronger surface 54.

In a preferred embodiment of the present invention, the stronger surface 54 of the lens 50 has the values of: $A_2 = 0.000444$, $A_4 = 0.000001$, $A_6 = 0.0$, $C = -0.092$ and $cc = -0.933$; whereas the weaker surface 52 of the lens 50 has values of: $A_2 = -0.00243$, $A_4 = 0.0000012$, $A_6 = 0.0$, $C = 0.045$ and $cc = -1.213$.

While the diameter d of the lens 50 may be varied, the preferred diameter is 35 millimeters. The aspheric lens 50 produces a 60° field of view for the scanning laser ophthalmoscope 10 which is extremely wide compared to prior scanning laser ophthalmoscopes and ophthalmoscopes in general. Further, the real image produced by the aspheric lens 50 is substantially free from distortions.

Many modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. A portable scanning laser ophthalmoscope comprising:
   a housing that is sufficiently small to be carried by a clinician;
   a source of laser light contained in said housing;
   a scanning system positioned in said housing so as to receive laser light from said source for generating a two dimensional area of illumination from said laser light;
   a battery contained in said housing for providing power to said scanning system; and
   an optical system contained in said housing for directing the illumination from the scanning system to the patient's eye for illuminating the fundus thereof and said optical system intercepting light reflected from the patient's eye to generate a magnified image of the interior of the patient's eye, said optical system including an eyepiece lens through which a clinician looks to directly view said magnified image of the interior of the patient's eye.

2. A portable scanning laser ophthalmoscope as recited in claim 1 wherein said optical system includes a second lens disposed in said housing between said scanning system and said patient's eye for focusing said illumination light from said scanning system on an area generally proximate to the patient's pupil.

3. A portable scanning laser ophthalmoscope as recited in claim 1 wherein said optical system includes a second lens disposed in said housing between said scanning system and said patient's eye for receiving light reflected from said patient's eye and focusing said received light onto an image plane disposed between said second lens and said eyepiece lens.

4. A portable scanning laser ophthalmoscope as recited in claim 1 wherein said optical system includes a nonsymmetric aspheric lens disposed in the optical paths between said scanning system and the patient's eye and between said eyepiece lens and the patient's eye for focusing said illumination light from said scanning system on an area generally proximate to the patient's pupil and for receiving light reflected from said patient's eye and focusing said received light onto an image plane disposed between said aspheric lens and said eyepiece lens.

5. A scanning laser ophthalmoscope as recited in claim 1 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

6. A scanning laser ophthalmoscope as recited in claim 5 wherein said passive optical element is a cylindrical lens.

7. A scanning laser ophthalmoscope as recited in claim 1 wherein said laser light from said source is polarized in a first direction and further including a polarizer disposed between said eyepiece lens and said patient's eye, said polarizer being polarized in a second direction different from said first direction of polarization of said laser light to pass desired light to said eyepiece lens for viewing by the clinician.

8. A scanning laser ophthalmoscope as recited in claim 7 wherein said polarizer is polarized perpendicular to the polarization of said laser light.

9. A portable scanning laser ophthalmoscope as recited in claim 1 wherein said optical system includes a beam splitter disposed in the optical paths between the patient's eye and the scanning system and between the patient's eye and the eyepiece lens to separate said optical paths without blocking a chief ray from the patient's eye to the eyepiece lens.

10. A portable scanning laser ophthalmoscope comprising:
    a housing that is sufficiently small to be carried by a clinician;
    a source of laser light contained in said housing and polarized in a first direction;
    a scanning system positioned in said housing to receive laser light form said source for generating a two dimensional area of illumination from said laser light that is directed towards a patient's eye to illuminate the interior thereof;
    an eyepiece lens for receiving light reflected from said patient's eye and through which a clinician looks to directly view a magnified image of an interior of the patient's eye; and
    a polarizer disposed in a path of said light reflected from said patient's eye to said eyepiece lens, said polarizer being polarized in a second direction different from said first direction of the polarization of said laser light to pass desired reflected light to said eyepiece lens.

11. A portable scanning laser ophthalmoscope as recited in claim 10 wherein said optical system includes a second lens disposed in said housing between said scanning system and said patient's eye for focusing said illumination light from said scanning system on an area generally proximate to the patient's pupil.

12. A portable scanning laser ophthalmoscope as recited in claim 10 wherein said optical system includes a second lens disposed in said housing between said scanning system and said patient's eye for receiving light reflected from said patient's eye and focusing said received light onto an image plane disposed between said second lens and said eyepiece lens.

13. A portable scanning laser ophthalmoscope as recited in claim 10 wherein said optical system includes a nonsymmetric aspheric lens disposed in the optical paths between said scanning system and the patient's eye and between said eyepiece lens and the patient's eye for focusing said illumination light from said scanning system on an area generally proximate to the patient's pupil and for receiving light reflected from said patient's eye and focusing said received light onto an image plane disposed between said aspheric lens and said eyepiece lens.

14. A scanning laser ophthalmoscope as recited in claim 10 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

15. A scanning laser ophthalmoscope as recited in claim 14 wherein said passive optical element is a cylindrical lens.

16. A portable scanning laser ophthalmoscope comprising:
    a housing that is sufficiently small to be carried by a clinician;
    a source of laser light contained in said housing;

a passive, stationary optical element positioned in a path of said laser light from said source such that said light impinges on said passive optical element at a point, said optical element generating a line of light from said point of light impinging thereon;

a scanner for scanning said line of light in a direction perpendicular to the direction in which said line extends to generate a two dimensional area of illumination;

a battery contained in said housing for providing power to said scanner;

an optical system for directing said two dimensional area of illumination to the patient's eye to illuminate the fundus of the eye and said optical system intercepting light reflected from the patient's eye to generate a magnified image of the interior of the patient's eye, said optical system including an eyepiece lens through which a clinician looks to directly view said magnified image of the interior of the patient's eye.

17. An illumination system for a scanning laser ophthalmoscope as recited in claim 16 wherein said passive optical element is a cylindrical lens.

18. A portable scanning laser ophthalmoscope as recited in claim 16 wherein said optical system includes a second lens disposed in said housing between said scanning system and said patient's eye for focusing said illumination light from said scanning system on an area generally proximate to the patient's pupil.

19. A portable scanning laser ophthalmoscope as recited in claim 16 wherein said optical system includes a second lens disposed in said housing between said scanning system and said patient's eye for receiving light reflected from said patient's eye and focusing said received light onto an image plane disposed between said second lens and said eyepiece lens.

20. A portable scanning laser ophthalmoscope as recited in claim 16 wherein said optical system includes a nonsymmetric aspheric lens disposed in the optical paths between said scanning system and the patient's eye and between said eyepiece lens and the patient's eye for focusing said illumination light from said scanning system on an area generally proximate to the patient's pupil and for receiving light reflected from said patient's eye and focusing said received light onto an image plane disposed between said aspheric lens and said eyepiece lens.

21. A scanning laser ophthalmoscope as recited in claim 16 wherein said laser light from said source is polarized in a first direction and further including a polarizer disposed between said eyepiece lens and said patient's eye, said polarizer being polarized in a second direction different from said first direction of polarization of said laser light to pass desired light to said eyepiece lens for viewing by the clinician.

22. A scanning laser ophthalmoscope as recited in claim 21 wherein said polarizer is polarized perpendicular to the polarization of said laser light.

23. A portable scanning laser ophthalmoscope as recited in claim 16 wherein said optical system includes a beam splitter disposed in the optical paths between the patient's eye and the scanner and between the patient's eye and the eyepiece lens to separate said optical paths without blocking a chief ray from the patient's eye to the eyepiece lens.

24. A portable scanning laser ophthalmoscope comprising:

a housing that is sufficiently small to be carried by a clinician;

a source of laser light contained in said housing;

a scanning system positioned in said housing so as to receive laser light from said source for generating a two dimensional area of illumination from said laser light that is directed towards a patient's eye to illuminate the interior thereof;

a battery contained in said housing for providing power to said scanning system; and an eyepiece lens system for receiving light reflected from the patient's eye and through which a clinician looks to directly view a magnified image of an interior portion of the patient's eye; and a nonsymmetric aspheric lens disposed in the optical paths between said scanning system and the patient's eye and between said eyepiece lens and the patient's eye for focusing said illumination light from said scanning system on an area generally proximate to the patient's pupil and for receiving light reflected from said patient's eye and focusing said received light onto an image plane disposed between said aspheric lens and said eyepiece lens.

25. A scanning laser ophthalmoscope as recited in claim 24 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

26. A scanning laser ophthalmoscope as recited in claim 25 wherein said passive optical element is a cylindrical lens.

27. A scanning laser ophthalmoscope as recited in claim 24 wherein said laser light from said source is polarized in a first direction and further including a polarizer disposed between said eyepiece lens and said patient's eye, said polarizer being polarized in a second direction different from said first direction of polarization of said laser light to pass desired light to said eyepiece lens for viewing by the clinician.

28. A scanning laser ophthalmoscope as recited in claim 27 wherein said polarizer is polarized perpendicular to the polarization of said laser light.

29. A portable scanning laser ophthalmoscope comprising:

a housing that is sufficiently small to be carried by a clinician;

a source of laser light contained in said housing;

a scanning system positioned in said housing so as to receive laser light from said source for generating a two dimensional area of illumination from said laser light that is directed towards a patient's eye to illuminate the interior thereof;

a battery contained in said housing for providing power to said scanning system; and a beam splitter disposed in the optical paths between the patient's eye and the scanning system and between the patient's eye and the eyepiece lens to separate said optical paths without blocking a chief ray from the patient's eye to the eyepiece lens.

30. A portable scanning laser ophthalmoscope as recited in claim 29 wherein said optical system includes a second lens disposed in said housing between said scanning system and said patient's eye for focusing said illumination light from said scanning system on an area generally proximate to the patient's pupil.

31. A portable scanning laser ophthalmoscope as recited in claim 29 wherein said optical system includes a second lens disposed in said housing between said scanning system and said patient's eye for receiving light reflected from said patient's eye and focusing said received light onto an image plane disposed between said second lens and said eyepiece lens.

32. A portable scanning laser ophthalmoscope as recited in claim 29 wherein said optical system includes a nonsymmetric aspheric lens disposed in the optical paths between said scanning system and the patient's eye and between said eyepiece lens and the patient's eye for focusing said illumination light from said scanning system on an area generally proximate to the patient's pupil and for receiving light reflected from said patient's eye and focusing said received light onto an image plane disposed between said aspheric lens and said eyepiece lens.

* * * * *

UNITED STATES PATENT AND TRADEMARK OFFICE
CERTIFICATE OF CORRECTION

PATENT NO. : 5,673,097
DATED : September 30, 1997
INVENTOR(S) : Gregory L. Heacock It is certified that error appears in the above-indentified patent and that said Letters Patent is hereby corrected as shown below:

Column 8, claim 10, line 14, delete "form" and insert -- from -- therefore.

Signed and Sealed this

Sixteenth Day of June, 1998

Attest:

BRUCE LEHMAN

Attesting Officer

Commissioner of Patents and Trademarks